United States Patent [19]

Thrower et al.

[11] Patent Number: 5,111,990

[45] Date of Patent: May 12, 1992

[54] INERTIA WELD NOTCH CONTROL THROUGH THE USE OF DIFFERENTIAL WALL THICKNESSES

[75] Inventors: Jack S. Thrower, West Palm Beach; Dennis C. Stewart, Palm City; Enrique E. Montero, Okeechobee, all of Fla.

[73] Assignee: United Technologies Corporation, Hartford, Conn.

[21] Appl. No.: 286,912

[22] Filed: Dec. 20, 1988

[51] Int. Cl.⁵ .............................................. B23K 20/12
[52] U.S. Cl. ..................................... 228/113; 228/119
[58] Field of Search ................. 228/112, 113, 114, 2, 228/263.13, 119, 222

[56] References Cited

U.S. PATENT DOCUMENTS

| | | | |
|---|---|---|---|
| 3,234,644 | 2/1966 | Hollander | 29/470.3 |
| 3,235,162 | 2/1966 | Hollander | 29/470.3 |
| 3,421,201 | 1/1969 | Oberle et al. | 228/113 |
| 3,462,826 | 8/1969 | Farmer et al. | 29/470.3 |
| 3,465,545 | 9/1969 | Stamm | 228/112 |
| 3,504,425 | 4/1970 | Sutovsky et al. | 228/112 |
| 3,571,905 | 3/1971 | Calton et al. | 228/113 |
| 3,576,067 | 4/1971 | Loyd | 228/113 |
| 3,591,068 | 7/1971 | Farmer et al. | 228/2 |
| 3,618,196 | 11/1971 | Sluetz | 228/113 |
| 4,365,136 | 12/1982 | Gottlieb | 219/121 |

FOREIGN PATENT DOCUMENTS

| | | | |
|---|---|---|---|
| 41873 | 10/1980 | Japan | 228/112 |
| 123488 | 6/1986 | Japan | 228/112 |

OTHER PUBLICATIONS

Kiwalle, Jozef, "Designing for Inertia Welding", Caterpiller Tractor Co., The Penton Publishing Co., Ohio, 1968.

Andreev, V. F., and Voinov, V. P., "Equipment for Restoring Automobile Components by Friction Welding", Welding Production (GB), vol. 20, No. 3, Mar. 1973.

AMF Friction Welding—The Basic Process, Brochure, 1970's.

AMF Friction Welding Application, Brochure, 1970's.

*Primary Examiner*—Samuel M. Heinrich
*Attorney, Agent, or Firm*—Charles E. Sohl

[57] ABSTRACT

A method is disclosed for controlling the magnitude and location of the weld notch which results from inertia welding of certain materials, such as superalloys. By controlling the size and geometry of the articles being joined a curved weld zone will result and the material expelled from the weld zone which produces the weld notch will be directed in a fashion which moves the weld notch outside of the original diameter of the articles being joined. The resultant welded article consisting of a larger portion and a smaller portion can be machined to the size of the smaller portion without any residual weld notch.

1 Claim, 2 Drawing Sheets

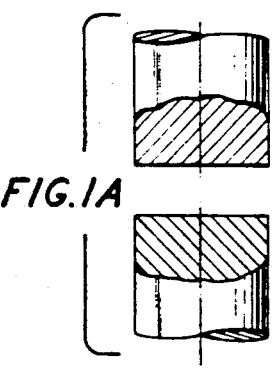
FIG. IA
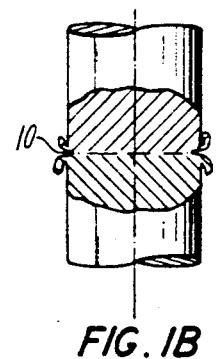
FIG. IB
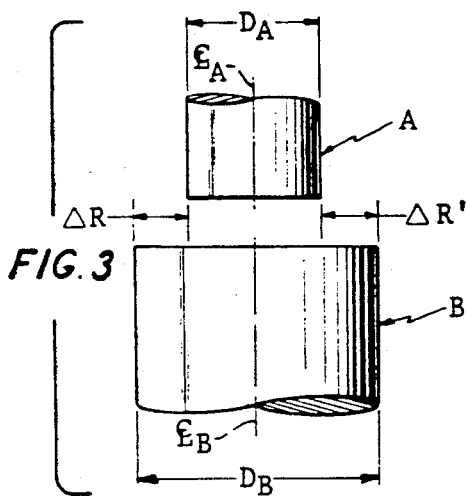
FIG. 3
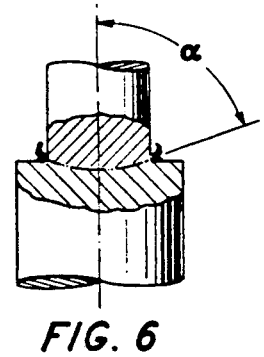
FIG. 6
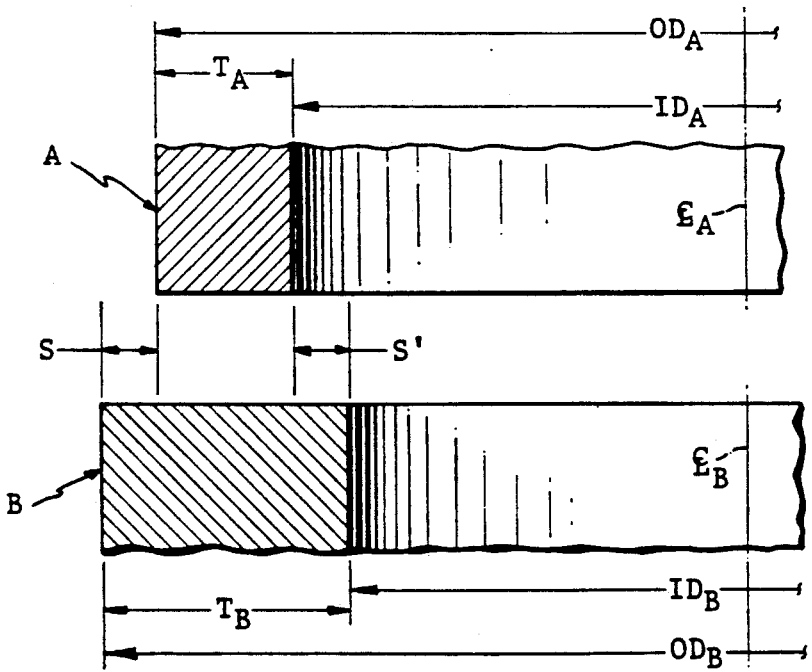
FIG. 4

13X

20 X

INERTIA WELD NOTCH CONTROL THROUGH THE USE OF DIFFERENTIAL WALL THICKNESSES

DESCRIPTION

1. Technical Field

This invention relates to the inertia welding of articles, especially hollow articles such as tubes. This invention also relates to the inertia welding of high strength superalloy articles and to the welding of high strength superalloy articles produced by powder metallurgy. This invention also relates to the repair of superalloy articles by inertia welding.

2. Background Art

Inertia welding is a process used to join metallic articles which are generally symmetrical about an axis of rotation. Such articles may be solid or hollow. Thus for example inertia welding can be used to join components together to form an article such as a crankshaft or a welded hollow tube assembly. The inertia welding process is described for example in U.S. Pat. Nos. 3,234,644; 3,235,162; 3,462,826; 3,591,068; and 4,365,136 which are incorporated herein by reference.

Briefly, in inertia welding the articles to be joined are located and positioned so that their axes of symmetry coincide and the surfaces to be joined are in a parallel relationship. One of the articles is held stationary, the other is attached to a rotatable flywheel. The rotatable article - flywheel combination is accelerated to a predetermined rotational speed and the rotating article is then forced against the stationary article. The flywheel geometry, mass and rotational speed determine the available kinetic energy, and this kinetic energy is dissipated (converted into thermal energy) by friction between the articles to be joined. The articles are forced together. The kinetic energy is sufficient to cause localized softening. When the flywheel rotation stops, the force between the articles is maintained or increased causing the softened portions of the articles to bond together. The force between the articles causes plastic or superplastic deformation in the weld zone. Cooling of the weld zone is fairly rapid by conduction of heat into the articles.

This is a desirable process having several non-obvious advantageous features including the fact that the process is conducted under conditions which cause expulsion of a significant amount of material from the weld zone thus inherently removing all detrimental surface contamination. The weld zone in the final article is more characteristic of a forging rather than a casting. Weld zones produced by other forms of welding such as laser, electron beam and electric fusion welding have weld zones which have been melted and resolidified and, therefore, the weld zones have characteristics of casting which is generally less desirable than the characteristics of a forging which are approached by the inertia welding weld zone.

Inertia welding is a form of friction welding. Another form of friction welding relies on a continuous motor drive to provide frictional heating rather than the energy stored in a flywheel. As used herein the term inertia welding includes other forms of rotational friction welding.

Inertia welding was developed and has been widely used in joining ferrous materials such as iron and steel in the heavy construction equipment industry. Recently it has been employed with reasonable success in joining superalloys. The joining of superalloy materials is much more demanding than the joining of ferrous materials since superalloys have higher softening temperature and are much more resistant to deformation at high temperatures. Inertia welding of "powder processed" superalloys are the most difficult of all inertia welding applications. The zone in the articles to be joined, which is to be softened by the welding process, is limited and the degree of upset or deformation in the weld zone is similarly limited. Consequently, in the inertia welding of (powder processed) superalloys there is generally a residual notch observed at the weld zone. Such a notch is not often observed in inertia welding of ferrous materials.

Unfortunately, in the case of powder processed nickel superalloys the weld zone notch invariably extends inwardly beyond the depth of the inertia weld zone. Thus, even after the weld upset is removed by machining there a notch usually remains and removal of the notch requires machining to less than the original diameters of the articles which were joined If the notch is not fully removed, it acts as a stress riser and as a failure initiation site during subsequent use of the welded article or even during the subsequent heat treatment. This notch problem is particularly detrimental in higher strength superalloys i.e. those having yield strengths in excess of 100 ksi at 1000° F.) metallurgy techniques. Superalloys are defined as nickel base alloys strengthened by gamma prime ($Ni_3Al$) precipitation.

Accordingly it is an object of the invention to describe a method for inertia welding materials and controlling the depth and location of the weld zone notch.

It is another object of the invention to disclose a method of inertia welding high strength (and/or powder metallurgy processed) superalloys while minimizing the deleterious effects of the weld zone notch.

Finally it is an object of the invention to disclose a method for using inertia welding to repair superalloy articles.

DISCLOSURE OF INVENTION

According to the present invention the notch which results from inertia welding has its size and position controlled by causing the articles to be joined to have significantly different dimension, different diameters in the case of solid stock or different wall thicknesses in the case of hollow articles.

The relative dimensions of the articles to be joined have a significant effect on heat flow from the weld zone and by apportioning the heat flow differently between the articles being joined, significant modification and control of the weld joint geometry occurs. Specifically, the smaller article reaches a higher temperature because the heat flow away from the weld zone into the thin article is less than that into the thicker article. Consequently the thin article undergoes more deformation and contributes more material to the weld zone expulsion, causing the weld zone notch to be moved relative to the position it would have been in had the articles had the same dimensions. The thicker article also provides compressive stresses and this alters the weld notch geometry. In articles produced according to the invention the weld zone displays significant curvature, concave with respect to the thinner component.

The foregoing and other features and advantages of the present invention will become more apparent from the following description and accompanying drawings.

BRIEF DESCRIPTION OF DRAWINGS

FIG. 1 is a schematic illustrating prior art inertial welding of two solid articles having the same diameters. FIG. 1A shows the articles before joining and FIG. 1B shows the articles after joining and shows the presence of a notch in the weld zone. The weld zone is essentially flat.

FIG. 3 illustrates the geometry parameters of a joint between two solid articles.

FIG. 4 illustrates the geometry parameters of a joint between two hollow articles.

FIG. 6 is a schematic of a welded article produced by the invention showing a curved weld zone.

BEST MODE FOR CARRYING OUT THE INVENTION

Figure 2:
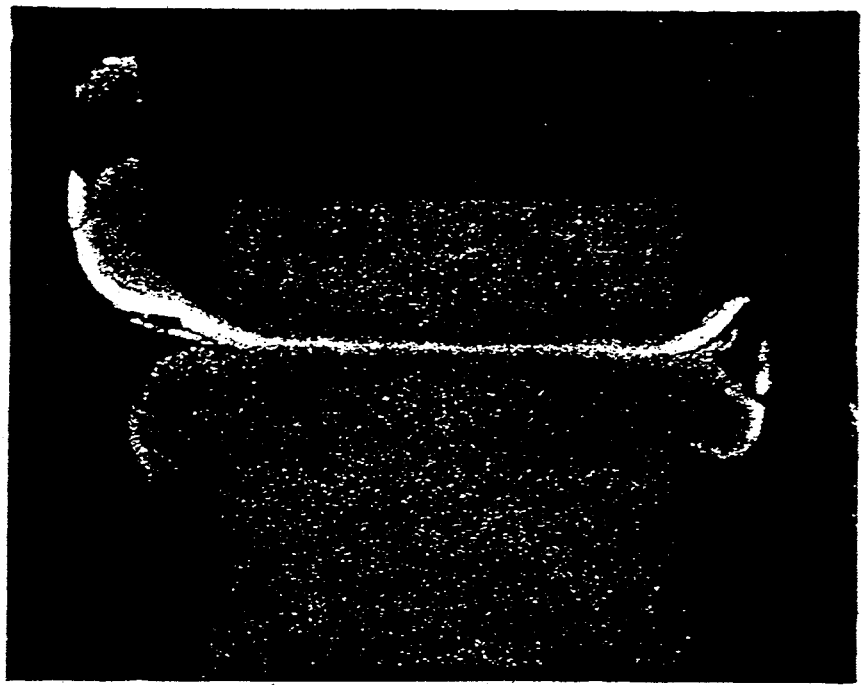
FIG. 2 is a photomacrograph showing a cross section of an actual inertial welded joint between two hollow articles of the same wall thickness illustrating the notch problem in the weld zone.

The invention will be described through reference to the accompanying figures which comprise drawings and photographs illustrating the prior art and the invention. FIG. 1 shows a schematic representation of solid superalloy articles of conventional geometry prior to and after inertia welding. FIG. 1A shows the articles prior to welding. FIG. 1B shows the articles after inertia welding and shows a notch 10 at a weld zone, a notch which penetrates into the article a distance below the original diameter of the article. Thus the weld zone area is less than the area of the articles which were joined. FIG. 2 is a 32× photomacrograph of identical wall thickness articles after inertia welding. This photomacrograph shows the weld zone and the notch which extends inward of the original diameter of the pieces being joined. Note that the weld zone is flat.

The essence of the present invention is the use of dissimilar mating article geometries in inertia welding. This is in contrast to the prior art which has to our knowledge used similar mating geometries for welding components of the same or similar alloy.

The invention weld zone geometries, prior to welding, are shown in and discussed with respect to FIGS. 3 and 4. FIG. 3 illustrates a solid article being joined to a solid article according to the invention. In FIG. 3 article A is to be joined to article B and article A has a smaller diameter $D_a$ than article B whose diameter is $D_b$. The articles must be located symmetrically relative to one another meaning that the center line of A $CL_a$ should coincide with the center line of B, $CL_b$. This is a normal requirement of inertia welding. Assuming that $CL_a$ is coincident with $CL_b$ the articles have a difference in radius, $\Delta R$ and $\Delta R'$ which are equal to $D_a$ minus $D_b$ divided by 2. Obviously $\Delta R$ and $\Delta R'$ will be equal and equal to the aforementioned value when $CL_a$ and $CL_b$ are coincident.

FIG. 4 shows the joint geometry for the joining of hollow articles such as tubes according to the invention. Again article A is to be joined to article B and the article A and article B are both hollow articles having center lines $CL_a$ and $CL_b$ respectively. Again the center lines are preferably coincident. Article A has a wall thickness $T_a$ and article B has a larger wall thickness $T_b$. Article A has an inside diameter $Id_a$ and an outside diameter of $Od_a$ while article B has an inside diameter $Id_b$ and an outside diameter $Od_b$. S and S' denote the step which will be formed on article A is inertia welded to article B.

The gist of the invention is providing different dimensions, diameter, in the case of solid articles and wall thickness in the case of hollow articles, to control the position and extent of the residual weld zone notch and to produce a curved weld zone.

This differential geometry produces "steps" on each side of the weld zone. The step dimensions necessary to achieve the goals of the invention differ as a function of the material involved The necessary ratio of thicknesses and therefore the step dimensions ($\Delta R$, $\Delta R'$ or S, S' in FIGS. 3 and 4) will vary with material and are best determined by routine experimentation on the part of the skilled artisan.

For the particular case of a powder processed nickel base superalloy material (derived from a commercial superalloy material known as IN100 which has a nominal composition of 12% chromium, 18% cobalt, 3.2% molybdenum, 4.3% titanium, 5% aluminum, 0.8% vanadium, 0.02% boron, 0.06% zirconium, balance nickel) with a grain size of ASTM 10.5 or finer which has received a heat treatment including a solution treatment at 2065° F., an oil quench from that temperature, and a subsequent low temperature heat treatment including exposure to 1600° F., 1800° F., 1200° F., and 1400° F. and having a minimum yield strength at 1300° F. of 150 ksi, the ratio of $D_b$ to $D_a$ in FIG. 3 or $T_b$ to $T_a$ in FIG. 4 should be from about 1.5 to about 1.7. Thus, with reference to FIG. 4 and the joining of hollow articles of that material, a thin article having a wall thickness of 0.200 inch would advantageously be joined to a thick article having a wall thickness of 0.300 to 0.340 inch.

The invention will generally be applied to articles whose nominal diameters (the average of inside and outside diameters) are essentially equal so that therefore, the outer step S and the inner step S' shown in FIG. 4 will usually be essentially equal. It is entirely within the scope of invention however to have different steps between the inside and outside so long as both steps fall within the range of preferred step dimensions set by the previously mentioned ratio, 1.5 to 1.7 for the particular alloy previously described. Thus for example in joining a 0.200 inch wall thickness article, the range of wall thickness articles which can be advantageously joined is from 0.300 to 0.340 inch. This would result, in the case of articles having the same nominal diameters, in a preferred range of step dimensions from 0.050 to 0.070 inch. It is clearly within the scope of the invention to inertia weld articles whose dimensions are such that one step has a dimension S of 0.050 inch and the other step has a dimension S' of 0.070 inch.

By way of further example, material of the same composition as set forth above (that based on IN100) but given a different heat treatment which provides a lesser yield strength and greater elongation at elevated temperatures, has a desired ratio of thin to thick articles of 1.3 to 1.5. As previously stated the skilled artisan will be able to determine the ratio needed for other superalloy materials through the use of a relatively few number of experiments based on the information provided herein. We believe that the useful range will be between 1.2:1 and 2.0:1.

The invention is applicable to the situation where articles made of identical superalloys are to be welded. The invention is also applicable to the situation where equivalent superalloys are to be welded. The term equivalent means that the alloys have comparable high temperature properties It is well known that the high temperature properties (the properties near and above the recrystallization temperature) of superalloys are controlled by a variety of conditions including composition, grain size and prior heat treatment The term equivalent here means that the creep strength of the alloys to be joined are within 30% of each other when measured at a temperature midway between the recrystallization temperature and the melting temperature of the alloys. To be equivalent the superalloys must also have recrystallization and melting temperatures which are within 100° F. of each other.

Figure 5:
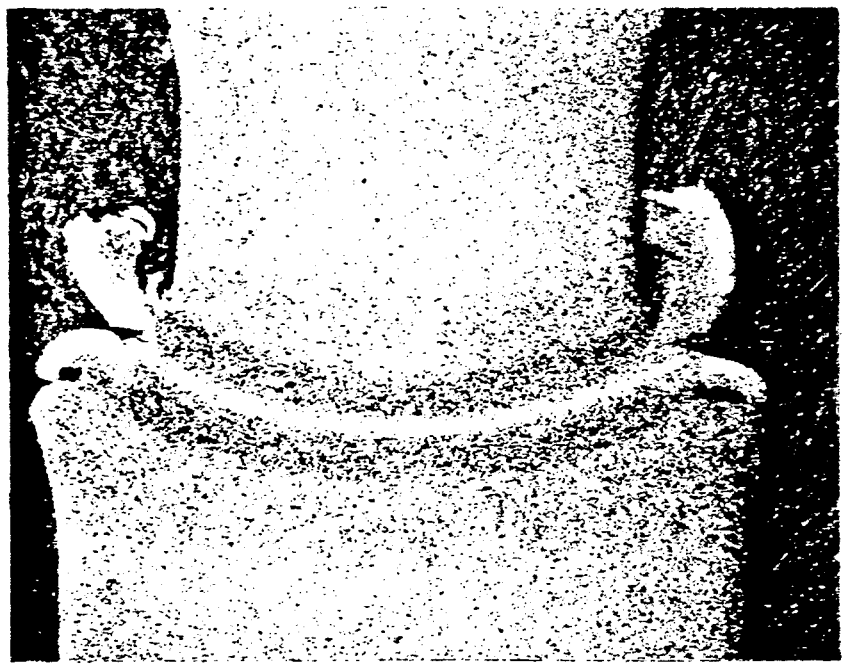
FIG. 5 is a photomacrograph of a joint made according to the invention between hollow articles.

FIG. 5 is a photomacrograph at 20× illustrating an inertia weld zone made according to the present invention illustrating that the weld zone notch does not penetrate below the original dimensions of the thinner article.

FIG. 5 illustrates a significant feature of articles inertia welded according to the invention. As can be seen in FIG. 5 the inertia weld zone has a significant degree of curvature. FIG. 5 can be contrasted with FIG. 2 which is another photomacrograph illustrating a conventional inertia weld showing a flat or planar weld zone. The curved inertia weld zone, shown in FIG. 5, is an important feature of the invention and the degree of curvature can be used as a guide for the skilled artisan in adapting the invention to different materials or other changed conditions. It is the curved inertia weld zone which causes the directed expulsion of material and contributes to the control of the residual weld notch location and magnitude.

As shown in FIG. 6 a tangent drawn to the curved inertia weld zone and projected back to the center line of the welded article (the axis of rotation) will produce an angle α of less than 90°. The angle α, as measured on the FIG. 5 photomacrograph, is approximately 70°. As another way of defining the present invention is to say that the invention benefits will be observed believed that when a tangent line drawn to the curved weld zone at the point where the curved weld zone terminates (the notch area) and projected back to the center line of the welded article forms an angle α of between about 50° and about 80°.

The utility of the present invention is high in the context of weld repairing damaged articles such as gas turbine engine components. Such damage may occur as a result of the in service use or may occur during fabrication as the result of machining errors. The general procedure is to remove the damaged portion from the non damaged portion by machining and then to replace the damaged portion with an undamaged portion of a proper geometry by inertia welding. The obvious requirement is that any residual weld zone notch not diminish the strength or utility of the article. As previously noted, inertia welding as practiced in the prior art would not meet this criteria (when welding high strength and/or powder metallurgy processed superalloy) since the notch at the weld zone would extend inwardly of the original diameter of the, machined to size, original undamaged portion of the welded article. The alternatives, each undesirable, were to tolerate a notch at the weld zone and/or to reduce the entire diameter of the article below that of the original design. It can readily be visualized that according to the present invention a thicker wall section piece could be welded onto a thin wall original, machined to size, section and that the weld zone notch could thereby be caused to be located outside of the original diameter thus permitting the oversize repair portion of the article to be machined to the original design size with the complete removal of the weld zone notch.

Although this invention has been shown and described with respect to detailed embodiments thereof, it will be understood by those skilled in the art that various changes in form and detail thereof may be made without departing from the spirit and scope of the claimed invention.

We claim:

1. A method for inertia weld repair of high strength superalloy articles which comprises:
   a) removal of a damaged portion of the article leaving a nondamaged portion;
   b) replacement of said damaged portion by inertia welding a replacement portion of an equivalent superalloy to the damage free portion, producing a residual notch in the weld zone, wherein said replacement is larger in cross section at the weld zone than said nondamaged portion and produces thereby a curved weld zone and so that the residual weld notch does not extend into the nondamaged portion;
   c) removal of the excess material from the replacement portion.

* * * * *